(12) United States Patent
Petersen (10) Patent No.: US 8,204,567 B2
(45) Date of Patent: Jun. 19, 2012

(54) SIGNAL DEMODULATION

(75) Inventor: Ethan Petersen, Castro Valley, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1222 days.

(21) Appl. No.: 11/955,824

(22) Filed: Dec. 13, 2007

(65) Prior Publication Data

US 2009/0154573 A1    Jun. 18, 2009

(51) Int. Cl.
*A61B 5/1455* (2006.01)
(52) U.S. Cl. ..................................... 600/336; 600/323
(58) Field of Classification Search .................. 600/310, 600/322–324, 326, 330–331, 336; 375/257
See application file for complete search history.

(56) References Cited

U.S. PATENT DOCUMENTS

| | | |
|---|---|---|
| 3,638,640 A | 2/1972 | Shaw |
| 4,714,341 A | 12/1987 | Hamaguri et al. |
| 4,800,885 A | 1/1989 | Johnson |
| 4,805,623 A | 2/1989 | Jöbsis |
| 4,807,631 A | 2/1989 | Hersh et al. |
| 4,832,484 A | 5/1989 | Aoyagi et al. |
| 4,911,167 A | 3/1990 | Corenman et al. |
| 4,913,150 A | 4/1990 | Cheung et al. |
| 4,936,679 A | 6/1990 | Mersch |
| 4,938,218 A | 7/1990 | Goodman et al. |
| 4,971,062 A | 11/1990 | Hasebe et al. |
| 4,972,331 A | 11/1990 | Chance |
| 4,974,591 A | 12/1990 | Awazu et al. |
| 5,028,787 A | 7/1991 | Rosenthal et al. |
| 5,065,749 A | 11/1991 | Hasebe et al. |
| 5,084,327 A | 1/1992 | Stengel |
| 5,094,239 A | 3/1992 | Jaeb et al. |
| 5,113,861 A | 5/1992 | Rother |
| 5,119,815 A | 6/1992 | Chance |
| 5,122,974 A | 6/1992 | Chance |
| 5,167,230 A | 12/1992 | Chance |
| 5,190,038 A | 3/1993 | Polson et al. |
| 5,246,003 A | 9/1993 | DeLonzor |
| 5,247,931 A | 9/1993 | Norwood |
| 5,263,244 A | 11/1993 | Centa et al. |
| 5,275,159 A | 1/1994 | Griebel |

(Continued)

FOREIGN PATENT DOCUMENTS

DE          19640807          10/1996

(Continued)

OTHER PUBLICATIONS

Aoyagi, T., et al.; "Analysis of Motion Artifacts in Pulse Oximetry," *Japanese Society ME*, vol. 42, p. 20 (1993) (Article in Japanese—contains English summary of article).

(Continued)

*Primary Examiner* — Eric Winakur
*Assistant Examiner* — Chu Chuan (JJ) Liu (57) ABSTRACT

A method for processing an analog composite signal in a system has the steps of receiving a composite signal with at least one first signal component and at least one interfering signal component; filtering the composite signal with a filter having a transfer function H(s); sampling the filtered composite signal in periodic intervals wherein each periodic interval has n samples; forming a matrix equation representing the composite signal wherein the matrix equation has a signal vector with the at least first one signal component and the at least one interfering signal component and a matrix comprising weighted coefficients; solving the matrix equation to determine the at least one signal component; outputting the at least one signal component.

20 Claims, 4 Drawing Sheets

U.S. PATENT DOCUMENTS

| | | | |
|---|---|---|---|
| 5,279,295 A | 1/1994 | Martens et al. | |
| 5,297,548 A | 3/1994 | Pologe | |
| 5,355,880 A | 10/1994 | Thomas et al. | |
| 5,372,136 A | 12/1994 | Steuer et al. | |
| 5,385,143 A | 1/1995 | Aoyagi | |
| 5,390,670 A | 2/1995 | Centa et al. | |
| 5,413,099 A | 5/1995 | Schmidt et al. | |
| 5,469,845 A | 11/1995 | DeLonzor et al. | |
| 5,482,036 A | 1/1996 | Diab et al. | |
| 5,483,646 A | 1/1996 | Uchikoga | |
| 5,553,614 A | 9/1996 | Chance | |
| 5,564,417 A | 10/1996 | Chance | |
| 5,575,285 A | 11/1996 | Takanashi et al. | |
| 5,611,337 A | 3/1997 | Bukta | |
| 5,630,413 A | 5/1997 | Thomas et al. | |
| 5,632,272 A * | 5/1997 | Diab et al. | 600/323 |
| 5,645,059 A | 7/1997 | Fein et al. | |
| 5,645,060 A | 7/1997 | Yorkey | |
| 5,680,857 A | 10/1997 | Pelikan et al. | |
| 5,692,503 A | 12/1997 | Keunstner | |
| 5,730,124 A | 3/1998 | Yamauchi | |
| 5,758,644 A | 6/1998 | Diab et al. | |
| 5,779,631 A | 7/1998 | Chance | |
| 5,782,757 A | 7/1998 | Diab et al. | |
| 5,786,592 A | 7/1998 | Hök | |
| 5,830,136 A | 11/1998 | Delonzor et al. | |
| 5,830,139 A | 11/1998 | Abreu | |
| 5,831,598 A | 11/1998 | Käuffert et al. | |
| 5,842,981 A | 12/1998 | Larsen et al. | |
| 5,871,442 A | 2/1999 | Madarasz et al. | |
| 5,873,821 A | 2/1999 | Chance et al. | |
| 5,920,263 A | 7/1999 | Huttenhoff et al. | |
| 5,995,855 A | 11/1999 | Kiani et al. | |
| 5,995,856 A | 11/1999 | Mannheimer et al. | |
| 5,995,858 A | 11/1999 | Kinast | |
| 5,995,859 A | 11/1999 | Takahashi | |
| 6,011,986 A | 1/2000 | Diab et al. | |
| 6,064,898 A | 5/2000 | Aldrich | |
| 6,081,742 A | 6/2000 | Amano et al. | |
| 6,088,607 A | 7/2000 | Diab et al. | |
| 6,120,460 A | 9/2000 | Abreu | |
| 6,134,460 A | 10/2000 | Chance | |
| 6,150,951 A | 11/2000 | Olejniczak | |
| 6,154,667 A | 11/2000 | Miura et al. | |
| 6,163,715 A | 12/2000 | Larsen et al. | |
| 6,181,958 B1 | 1/2001 | Steuer et al. | |
| 6,181,959 B1 | 1/2001 | Schöllermann et al. | |
| 6,230,035 B1 | 5/2001 | Aoyagi et al. | |
| 6,266,546 B1 | 7/2001 | Steuer et al. | |
| 6,285,895 B1 | 9/2001 | Ristolainen et al. | |
| 6,312,393 B1 | 11/2001 | Abreu | |
| 6,353,750 B1 | 3/2002 | Kimura et al. | |
| 6,397,091 B2 | 5/2002 | Diab et al. | |
| 6,415,236 B2 | 7/2002 | Kobayashi et al. | |
| 6,419,671 B1 | 7/2002 | Lemberg | |
| 6,438,399 B1 | 8/2002 | Kurth | |
| 6,461,305 B1 | 10/2002 | Schnall | |
| 6,466,809 B1 | 10/2002 | Riley | |
| 6,487,439 B1 | 11/2002 | Skladnev et al. | |
| 6,501,974 B2 | 12/2002 | Huiku | |
| 6,501,975 B2 | 12/2002 | Diab et al. | |
| 6,526,301 B2 | 2/2003 | Larsen et al. | |
| 6,544,193 B2 | 4/2003 | Abreu | |
| 6,546,267 B1 | 4/2003 | Sugiura et al. | |
| 6,549,795 B1 | 4/2003 | Chance | |
| 6,580,086 B1 | 6/2003 | Schulz et al. | |
| 6,591,122 B2 | 7/2003 | Schmitt | |
| 6,594,513 B1 | 7/2003 | Jobsis et al. | |
| 6,606,509 B2 | 8/2003 | Schmitt | |
| 6,606,511 B1 | 8/2003 | Ali et al. | |
| 6,615,064 B1 | 9/2003 | Aldrich | |
| 6,618,042 B1 | 9/2003 | Powell | |
| 6,622,095 B2 | 9/2003 | Kobayashi et al. | |
| 6,654,621 B2 | 11/2003 | Palatnik et al. | |
| 6,654,624 B2 | 11/2003 | Diab et al. | |
| 6,658,276 B2 | 12/2003 | Kianl et al. | |
| 6,658,277 B2 | 12/2003 | Wasserman | |
| 6,662,030 B2 | 12/2003 | Khalil et al. | |
| 6,668,183 B2 | 12/2003 | Hicks et al. | |
| 6,671,526 B1 | 12/2003 | Aoyagi et al. | |
| 6,671,528 B2 | 12/2003 | Steuer et al. | |
| 6,678,543 B2 | 1/2004 | Diab et al. | |
| 6,684,090 B2 | 1/2004 | Ali et al. | |
| 6,690,958 B1 | 2/2004 | Walker et al. | |
| 6,697,658 B2 | 2/2004 | Al-Ali | |
| 6,708,048 B1 | 3/2004 | Chance | |
| 6,711,424 B1 | 3/2004 | Fine et al. | |
| 6,711,425 B1 | 3/2004 | Reuss | |
| 6,714,245 B1 | 3/2004 | Ono | |
| 6,731,274 B2 | 5/2004 | Powell | |
| 6,785,568 B2 | 8/2004 | Chance | |
| 6,793,654 B2 | 9/2004 | Lemberg | |
| 6,801,797 B2 | 10/2004 | Mannheimer et al. | |
| 6,801,798 B2 | 10/2004 | Geddes et al. | |
| 6,801,799 B2 | 10/2004 | Mendelson | |
| 6,826,419 B2 | 11/2004 | Diab et al. | |
| 6,829,496 B2 | 12/2004 | Nagai et al. | |
| 6,850,053 B2 | 2/2005 | Daalmans et al. | |
| 6,863,652 B2 | 3/2005 | Huang et al. | |
| 6,873,865 B2 | 3/2005 | Steuer et al. | |
| 6,889,153 B2 | 5/2005 | Dietiker | |
| 6,898,451 B2 | 5/2005 | Wuori | |
| 6,939,307 B1 | 9/2005 | Dunlop | |
| 6,947,780 B2 | 9/2005 | Scharf | |
| 6,949,081 B1 | 9/2005 | Chance | |
| 6,961,598 B2 | 11/2005 | Diab | |
| 6,983,178 B2 | 1/2006 | Fine et al. | |
| 6,993,371 B2 | 1/2006 | Kiani et al. | |
| 6,996,427 B2 | 2/2006 | Ali et al. | |
| 7,003,339 B2 | 2/2006 | Diab et al. | |
| 7,024,235 B2 | 4/2006 | Melker et al. | |
| 7,027,849 B2 | 4/2006 | Al-Ali | |
| 7,030,749 B2 | 4/2006 | Al-Ali | |
| 7,035,697 B1 | 4/2006 | Brown | |
| 7,047,056 B2 | 5/2006 | Hannula et al. | |
| 7,127,278 B2 | 10/2006 | Melker et al. | |
| 7,162,306 B2 | 1/2007 | Caby et al. | |
| 7,209,775 B2 | 4/2007 | Bae et al. | |
| 7,221,971 B2 | 5/2007 | Diab et al. | |
| 7,236,811 B2 | 6/2007 | Schmitt | |
| 7,263,395 B2 | 8/2007 | Chan et al. | |
| 7,272,426 B2 | 9/2007 | Schmid | |
| 7,302,284 B2 | 11/2007 | Baker, Jr. et al. | |
| 7,315,753 B2 | 1/2008 | Baker, Jr. et al. | |
| 7,336,982 B2 | 2/2008 | Yoo | |
| 7,336,983 B2 | 2/2008 | Baker, Jr. et al. | |
| 7,343,187 B2 | 3/2008 | Stetson | |
| 7,373,193 B2 | 5/2008 | Al-Ali et al. | |
| 7,400,919 B2 | 7/2008 | Petersen et al. | |
| 2001/0005773 A1 | 6/2001 | Larsen et al. | |
| 2001/0020122 A1 | 9/2001 | Steuer et al. | |
| 2001/0039376 A1 | 11/2001 | Steuer et al. | |
| 2001/0044700 A1 | 11/2001 | Kobayashi et al. | |
| 2002/0026106 A1 | 2/2002 | Khalil et al. | |
| 2002/0035318 A1 | 3/2002 | Mannheimer et al. | |
| 2002/0038079 A1 | 3/2002 | Steuer et al. | |
| 2002/0042558 A1 | 4/2002 | Mendelson | |
| 2002/0049389 A1 | 4/2002 | Abreu | |
| 2002/0062071 A1 | 5/2002 | Diab et al. | |
| 2002/0111748 A1 | 8/2002 | Kobayashi et al. | |
| 2002/0133068 A1 | 9/2002 | Huiku | |
| 2002/0156354 A1 | 10/2002 | Larson | |
| 2002/0161287 A1 | 10/2002 | Schmitt | |
| 2002/0161290 A1 | 10/2002 | Chance | |
| 2002/0165439 A1 | 11/2002 | Schmitt | |
| 2002/0198443 A1 | 12/2002 | Ting | |
| 2003/0023140 A1 | 1/2003 | Chance | |
| 2003/0055324 A1 | 3/2003 | Wasserman | |
| 2003/0060693 A1 | 3/2003 | Monfre et al. | |
| 2003/0139687 A1 | 7/2003 | Abreu | |
| 2003/0144584 A1 | 7/2003 | Mendelson | |
| 2003/0220548 A1 | 11/2003 | Schmitt | |
| 2003/0220576 A1 | 11/2003 | Diab | |
| 2004/0010188 A1 | 1/2004 | Wasserman | |
| 2004/0054270 A1 | 3/2004 | Pewzner et al. | |
| 2004/0087846 A1 | 5/2004 | Wasserman | |
| 2004/0107065 A1 | 6/2004 | Al-Ali | |

| | | | |
|---|---|---|---|
| 2004/0127779 | A1 | 7/2004 | Steuer et al. |
| 2004/0171920 | A1 | 9/2004 | Mannheimer et al. |
| 2004/0176670 | A1 | 9/2004 | Takamura et al. |
| 2004/0176671 | A1 | 9/2004 | Fine et al. |
| 2004/0230106 | A1 | 11/2004 | Schmitt et al. |
| 2005/0010092 | A1* | 1/2005 | Weber et al. ............ 600/322 |
| 2005/0080323 | A1 | 4/2005 | Kato |
| 2005/0101850 | A1 | 5/2005 | Parker |
| 2005/0113651 | A1 | 5/2005 | Wood et al. |
| 2005/0113656 | A1 | 5/2005 | Chance |
| 2005/0143634 | A1 | 6/2005 | Baker, Jr. et al. |
| 2005/0168722 | A1 | 8/2005 | Forstner et al. |
| 2005/0177034 | A1 | 8/2005 | Beaumont |
| 2005/0192488 | A1 | 9/2005 | Bryenton et al. |
| 2005/0203357 | A1 | 9/2005 | Debreczeny et al. |
| 2005/0228248 | A1 | 10/2005 | Dietiker |
| 2005/0267346 | A1 | 12/2005 | Faber et al. |
| 2005/0283059 | A1 | 12/2005 | Iyer et al. |
| 2006/0009688 | A1 | 1/2006 | Lamego et al. |
| 2006/0015021 | A1 | 1/2006 | Cheng |
| 2006/0020181 | A1 | 1/2006 | Schmitt |
| 2006/0030763 | A1 | 2/2006 | Mannheimer et al. |
| 2006/0052680 | A1 | 3/2006 | Diab |
| 2006/0058683 | A1 | 3/2006 | Chance |
| 2006/0064024 | A1 | 3/2006 | Schnall |
| 2006/0195028 | A1 | 8/2006 | Hannula et al. |
| 2006/0224058 | A1 | 10/2006 | Mannheimer |
| 2006/0247501 | A1 | 11/2006 | Ali |
| 2006/0258921 | A1 | 11/2006 | Addison et al. |
| 2007/0149872 | A1 | 6/2007 | Zhang et al. |
| 2007/0225582 | A1 | 9/2007 | Diab et al. |
| 2008/0033265 | A1 | 2/2008 | Diab et al. |

FOREIGN PATENT DOCUMENTS

| | | |
|---|---|---|
| EP | 0630203 | 9/1993 |
| EP | 1491135 | 12/2004 |
| JP | 3170866 | 7/1991 |
| JP | 3238813 | 10/1991 |
| JP | 4191642 | 7/1992 |
| JP | 4332536 | 11/1992 |
| JP | 7124138 | 5/1995 |
| JP | 7136150 | 5/1995 |
| JP | 10216115 | 8/1998 |
| JP | 2003194714 | 7/2003 |
| JP | 2003210438 | 7/2003 |
| JP | 2003275192 | 9/2003 |
| JP | 2003339678 | 12/2003 |
| JP | 2004008572 | 1/2004 |
| JP | 2004113353 | 4/2004 |
| JP | 2004135854 | 5/2004 |
| JP | 2004194908 | 7/2004 |
| JP | 2004202190 | 7/2004 |
| JP | 2004248819 | 9/2004 |
| JP | 2004290545 | 10/2004 |
| WO | WO9221281 | 12/1992 |
| WO | WO9309711 | 5/1993 |
| WO | WO9403102 | 2/1994 |
| WO | WO9512349 | 5/1995 |
| WO | WO9749330 | 12/1997 |
| WO | WO9842249 | 10/1998 |
| WO | WO9842251 | 10/1998 |
| WO | WO9843071 | 10/1998 |
| WO | WO9932030 | 7/1999 |
| WO | WO0021438 | 4/2000 |
| WO | WO2005009221 | 2/2005 |
| WO | WO 2005009221 | 2/2005 |

OTHER PUBLICATIONS

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30-Nov. 2, 1997; pp. 2326-2329.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

East, Christine E., et al.; "Fetal Oxygen Saturation and Uterine Contractions During Labor," *American Journal of Perinatology*, vol. 15, No. 6, pp. 345-349 (Jun. 1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engin*.

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1999).

Kaestle, S.; "An Algorithm for Reliable Processing of Pulse Oximetry Signals Under strong Noise Conditions," *Dissertation Book*, Lubeck University, Germany (1999).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Kaestle, S.; "Determining Artefact Sensitivity of New Pulse Oximeters in Laboratory Using Signals Obtained from Patient," *Biomedizinische Technik*, vol. 45 (2000).

Cysewska-Sobusaik, Anna; "Metrological Problems With noninvasive Transillumination of Living Tissues," *Proceedings of SPIE*, vol. 4515, pp. 15-24 (2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

A. Johansson; "Neural network for photoplethysmographic respiratory rate monitoring," *Medical & Biological Engineering & Computing*, vol. 41, pp. 242-248 (2003).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sept.

Matsuzawa, Y., et al.; "Pulse Oximeter," *Home Care Medicine*, pp. 42-45 (Jul. 2004); (Article in Japanese—contains English summary of article).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

* cited by examiner

SIGNAL DEMODULATION

TECHNICAL FIELD

The technical field of the present application relates to oximeter signal processing.

BACKGROUND

Pulse oximeters are used to indirectly measures the amount of oxygen in a patient's blood and for measuring the pulse of a patient. Furthermore, they can be used to measure changes in blood volume in the skin, producing a photoplethysmograph. Pulse oximeters are usually attached to a medical monitor so staff can see a patient's oxygenation at all times. Most monitors also display in addition the heart rate.

A pulse oximeter is a particularly convenient non-invasive measurement instrument. Typically it has a pair of small light-emitting diodes (LEDs) facing a photodiode through a translucent part of the patient's body, usually a fingertip or an earlobe. One LED is red, with wavelength of approximately 660 nm, and the other is infrared, using a wavelength of approximately 905, 910, or 940 nm. Absorption at these wavelengths differs significantly between oxyhemoglobin and its deoxygenated form, therefore from the ratio of the absorption of the red and infrared light the oxy/deoxyhemoglobin ratio can be calculated.

The monitored signal is modulated by the heart beat because the arterial blood vessels expand and contract with each heartbeat. Oximeters are furthermore subject to various interferences. For example, ambient light, in particular light emitted from fluorescent lighting, can introduce a significant interfering signal. Capacitive coupling in the patient cable between the LED wires and the detector wires is also a large source of additional errors. Generally on the rising and falling edges of the LED voltage an impulse current appears in the detector lines due to this capacitive coupling.

SUMMARY

According to an embodiment, a method for processing an analog composite signal in a system, may comprise the steps of: receiving a composite signal comprising at least one first signal component and at least one interfering signal component; filtering the composite signal with a filter having a transfer function H(s); sampling the filtered composite signal in periodic intervals wherein each periodic interval comprises n samples; forming a matrix equation representing the composite signal wherein the matrix equation comprises a signal vector comprising the at least first one signal component and the at least one interfering signal component and a matrix comprising weighted coefficients; solving the matrix equation to determine the at least one signal component; and outputting the at least one signal component.

According to a further embodiment, an interfering signal component can be approximated by a linear approximation between a first and last sample of each periodic interval. According to a further embodiment, the weighted coefficients for a transient interfering signal component can be determined by the transfer function and a sample position within a periodic interval. According to a further embodiment, the system can be an oximeter system comprising an oximeter sensor generating a Red signal component and an Infrared (IR) signal component as signal components, wherein an ambient light signal component and cable transients may be interfering signal components. According to a further embodiment, the ambient light signal component may be approximated by a linear approximation between a first and last sample of each periodic interval. According to a further embodiment, the weighted coefficients for the cable transients may be determined by the transfer function and a sample position within a periodic interval. According to a further embodiment, the Red signal component and the IR signal component may be timely separated within each periodic interval and the Red signal component and the IR signal component each may comprise a predetermined signal length having an on and off transient. According to a further embodiment, the ambient light signal component may be approximated by a linear approximation between a first and last sample of each periodic interval and the weighted coefficients for the cable transients are determined by the transfer function and a sample position within a periodic interval, and wherein a coefficient matrix may comprise first and second coefficients for the linear approximation, switch on and switch off coefficients for the cable transients, a Red coefficient, and an IR coefficient.

According to another embodiment, a system for processing an analog composite signal comprising at least one first signal component and at least one interfering signal component, may comprise: a filter having a transfer function H(s) receiving the composite signal and outputting a filtered composite signal; an analog-to-digital converter receiving the filtered composite signal and sampling the filtered composite signal in periodic intervals wherein each periodic interval comprises n samples; and a signal processor receiving the sampled filtered composite signal, wherein the signal processor forms a matrix equation representing the composite signal wherein the matrix equation comprises a signal vector comprising the at least first one signal component and the at least one interfering signal component and a matrix comprising weighted coefficients, wherein the signal processor is furthermore operable to solve the matrix equation to calculate the at least one signal component and to output the at least one signal component.

According to a further embodiment, an interfering signal may be approximated by a linear approximation between a first and last sample of each periodic interval. According to a further embodiment, the weighted coefficients for a transient interfering signal component may be determined by the transfer function and a sample position within a periodic interval. According to a further embodiment, the system can be an oximeter system comprising an oximeter sensor generating a Red signal component and an Infrared (IR) signal component as signal components, wherein an ambient light signal component and cable transients are interfering signal components. According to a further embodiment, the ambient light signal component may be approximated by a linear approximation between a first and last sample of each periodic interval. According to a further embodiment, the weighted coefficients for the cable transients may be determined by the transfer function and a sample position within a periodic interval. According to a further embodiment, the Red signal component and the IR signal component may be timely separated within each periodic interval and the Red signal component and the IR signal component each may comprise a predetermined signal length having an on and off transient. According to a further embodiment, the ambient light signal component may be approximated by a linear approximation between a first and last sample of each periodic interval and the weighted coefficients for the cable transients may be determined by the transfer function and a sample position within a periodic interval, wherein a coefficient matrix may comprise first and second coefficients for the linear approximation, switch on and switch off coefficients for the cable transients, a Red coefficient, and an IR coefficient.

According to yet another embodiment, an oximeter system may comprise an oximeter sensor generating an output signal with a Red signal component and an Infrared (IR) signal component which are timely separated within a periodic interval wherein the Red signal component and the IR signal component each comprise a predetermined signal length having an on and off transient, a filter having a transfer function H(s) receiving a composite signal consisting of the oximeter sensor output signal and at least one interfering signal component, wherein the filter outputs a filtered composite signal; an analog-to-digital converter receiving the filtered composite signal and sampling the filtered composite signal in periodic intervals wherein each periodic interval comprises n samples; and a signal processor receiving the sampled filtered composite signal, wherein the signal processor forms a matrix equation representing the composite signal wherein the matrix equation comprises a signal vector comprising the Red and IR signal components and the at least one interfering signal component and a matrix comprising weighted coefficients, wherein the signal processor is furthermore operable to solve the matrix equation to calculate the Red and IR signal components and to output the Red and IR signal components.

According to a further embodiment, an ambient light signal component and cable transients may be interfering signal components. According to a further embodiment, the ambient light signal component may be approximated by a linear approximation between a first and last sample of each periodic interval. According to a further embodiment, the weighted coefficients for the cable transients may be determined by the transfer function and a sample position within a periodic interval. According to a further embodiment, the ambient light component may be approximated by a linear approximation between a first and last sample of each periodic interval and the weighted coefficients for the cable transients are determined by the transfer function and a sample position within a periodic interval, wherein a coefficient matrix may comprise first and second coefficients for the linear approximation, switch on and switch off coefficients for the cable transients, a Red coefficient, and an IR coefficient.

According to yet another embodiment, a method for processing an analog composite signal in an oximeter system, may comprise the steps of: receiving a composite signal comprising at Red signal component and an infrared (IR) signal component from an oximeter sensor and at least one interfering signal component; filtering the composite signal with a filter having a transfer function H(s); sampling the filtered composite signal in periodic intervals wherein each periodic interval comprises n samples; forming a matrix equation representing the system wherein the matrix equation comprises a signal vector comprising the Red and IR signal component and the at least one interfering signal component and a matrix comprising weighted coefficients; solving the matrix equation to calculate the Red and IR signal components; and outputting the Red and IR signal components.

According to a further embodiment, an ambient light signal component and cable transients may be interfering signal components, wherein the ambient light can be approximated by a linear approximation between a first and last sample of each periodic interval and wherein the weighted coefficients for the cable transients may be determined by the transfer function and a sample position within a periodic interval. According to a further embodiment, the Red signal component and the IR signal component can be timely separated within each periodic interval and the Red signal component and the IR signal component each may comprise a predetermined signal length having an on and off transient. According to a further embodiment, the ambient light can be approximated by a linear approximation between a first and last sample of each periodic interval and the weighted coefficients for the cable transients are determined by the transfer function and a sample position within a periodic interval, and wherein a coefficient matrix comprises first and second coefficients for the linear approximation, switch on and switch off coefficients for the cable transients, a Red coefficient, and an IR coefficient.

Other technical advantages of the present disclosure will be readily apparent to one skilled in the art from the following figures, descriptions, and claims. Various embodiments of the present application obtain only a subset of the advantages set forth. No one advantage is critical to the embodiments.

BRIEF DESCRIPTION OF THE DRAWINGS

A more complete understanding of the present disclosure and advantages thereof may be acquired by referring to the following description taken in conjunction with the accompanying drawings, in which like reference numbers indicate like features, and wherein.

DETAILED DESCRIPTION

As stated above, oximeter detectors are subject to a variety of interfering signals. Currently the largest source of error in the electronics of a pulse oximeter arises from capacitive coupling in the patient cable between the LED wires and the detector wires. On the rising and falling edges of the LED voltage an impulse current appears in the detector lines due to this capacitive coupling. For example, it has been determined that the error in measured photo current due to such impulse currents can be up to around 71 pA, for example, out of a batch of 17 new cables. Older cables that have been worn will have compromised shields that could result in a much larger error.

Figure 1:
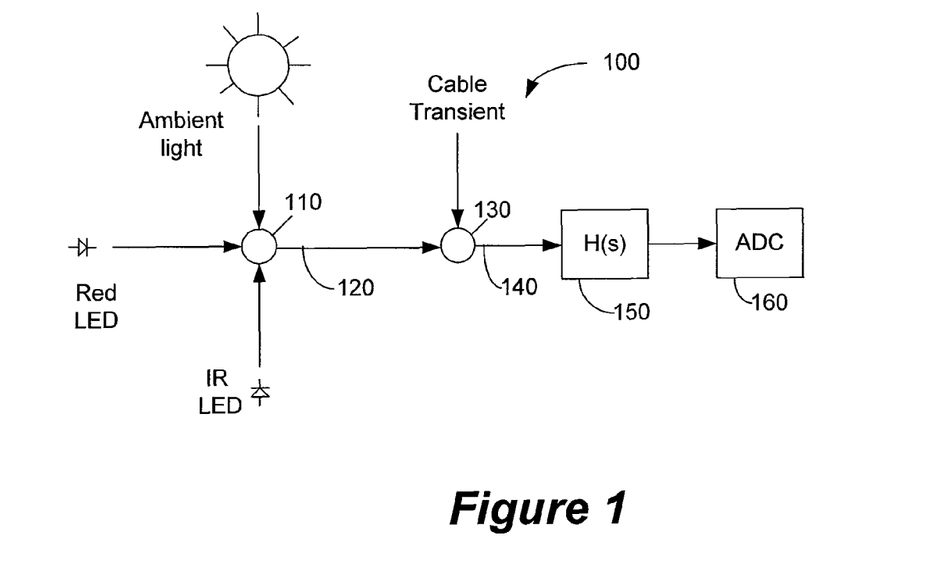
FIG. 1 is a block diagram of a typical oximeter arrangement, and the sources of interfering signals.

FIG. 1 shows a block diagram explaining the influences of the main interfering sources in oximeter systems. Generally, an oximeter sensor comprises a red LED and IR LED whose emitted light is passed through a patient's tissue. A detector receives these signals but also receives some ambient light as shown on the left side of FIG. 1. Node 110 simulates a summing point within the photo detector or detectors of an oximeter system. Thus, the photo detector produces a signal 120 which comprises the RED component, the IR component, and an ambient light component. Node 130 simulates the summing point of capacitive cable transient signals introduced into the detector signal. Thus, output signal 140 now comprises in addition to the signals mentioned above, the cable transient signals. Signal 140 is then fed into filter 150 comprising a transfer function H(s). The output signal of filter 150 is then fed to an analog-to-digital-converter 160.

Figure 2:
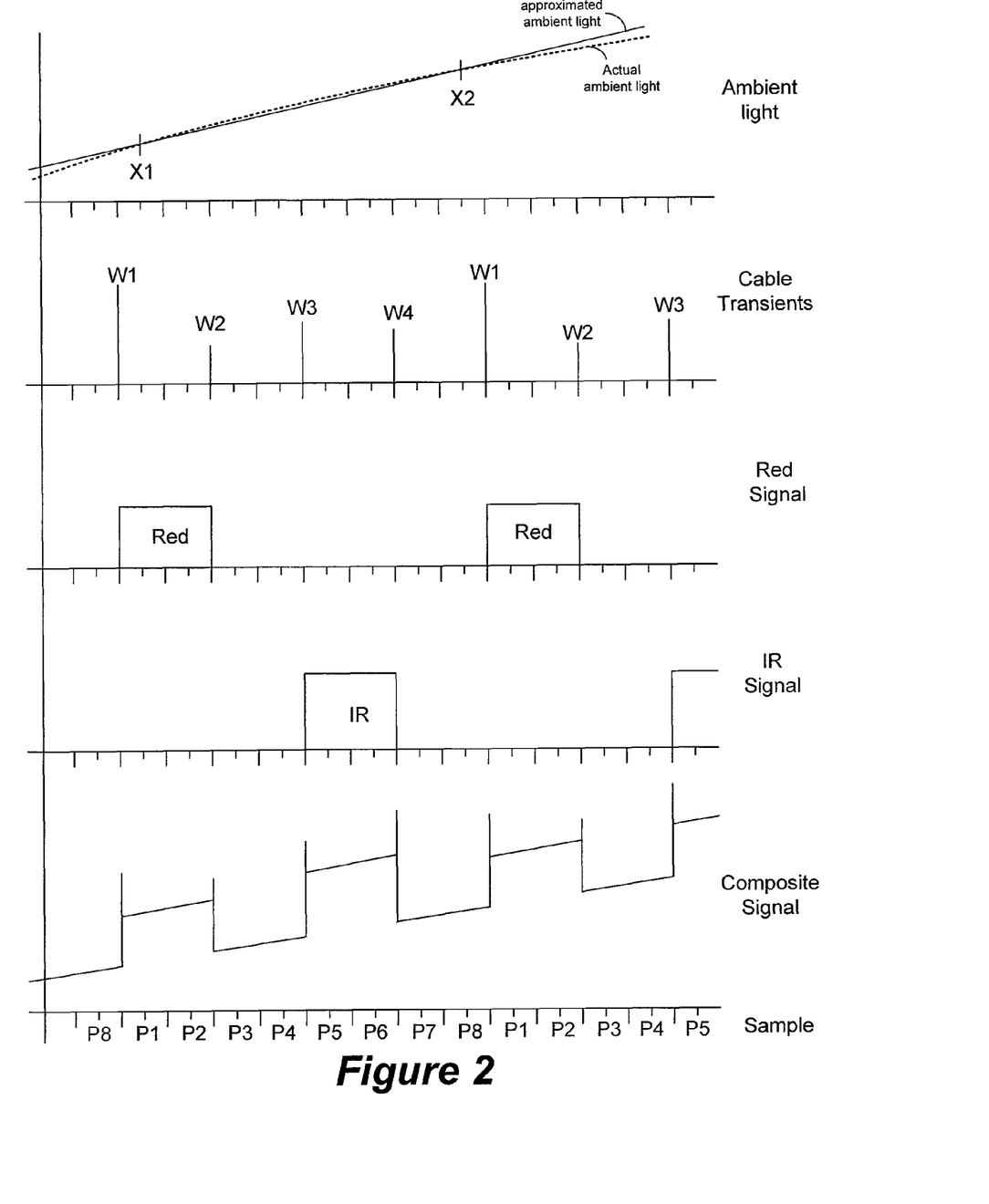
FIG. 2 depicts the various components of an oximeter input signal.

FIG. 2 shows exemplary signal curves for each signal component as shown in FIG. 1 as well as the composite signal. For each Red and IR signal pulse, according to an embodiment, 8 samples P1 . . . 8 are taken as indicated on the bottom x-axis. During the time frame P1 . . . 8, the ambient light, shown as the dotted line which can be dominated by components of the 50 Hz/60 Hz power line signals, is approximated by a linear line as shown in the top curve between points X1 and X2. The transient pulses caused by the rising and falling edges of the Red and IR signals are shown as signals W1, W2, W3, and W4. Next follows the Red signal and then the IR signal. The bottom curve represents the composite signal as it is fed to the filter 150. This composite signal represents a sum of the above signals.

This signal is then sampled by an analog-to-digital converter 160 as indicated at the bottom line of FIG. 2. As shown in FIG. 2, 8 samples are produced for each Red and IR pulse. However, according to other embodiments, more than eight samples can be generated which will improve performance. The composite signal which is filtered by filter 150 and sampled by analog-to-digital-converter 160 comprises the component signals as discussed with respect to FIG. 3. Thus, each component signal is first filtered before it is sampled by analog-to-digital converter 160. The filter is used for anti-aliasing and to help eliminate out of band noise. Thus, the filter 150 has a transfer function of H(s) that spreads out the composite signal in the time domain. Since the filter 150 is a linear system, each of the components can be analyzed by assuming they have all gone through the filter independently. The result is that an impulse will have energy spread across all the sample periods.

Figure 3:
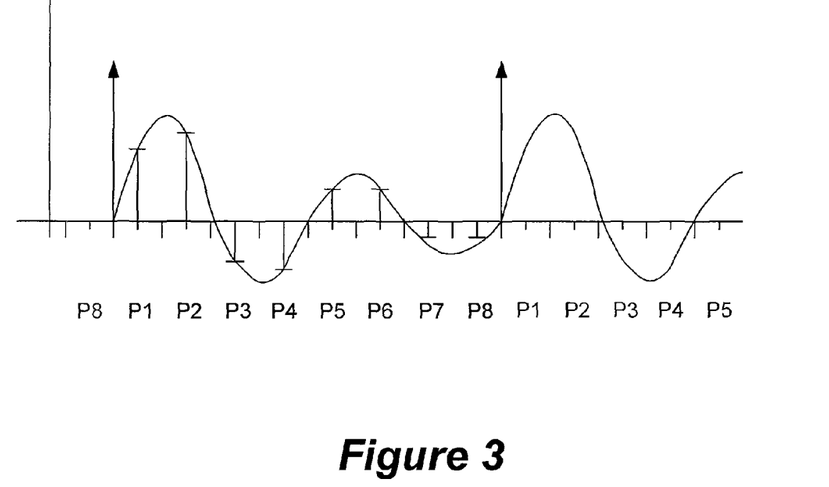
FIG. 3 an example of the impulse response of a filter to a chain of impulses.

FIG. 3 shows an exemplary output signal from signal filter 150 to which a series of periodic pulses W1 is fed. The respective sample points P1 . . . 8 produced by the analog-to-digital-converter 160 resulting from the pulses W1 fed to filter 150 are shown in FIG. 3 by the vertical lines ending with a crossbar. The magnitude of the sample at each sampling point is, thus, a function of the magnitude of the impulse W1 and the impulse response of the system. Since the time between the impulse W1 and the sample time is constant, the size of the sample at P1 is a constant times the magnitude of the impulse. This results in:

$$P1 = k1 \cdot W1$$
$$P2 = k2 \cdot W1$$
$$P3 = k3 \cdot W1$$
$$\vdots$$
and so on.

The results for the Red and IR components of the composite signal can be represented in a similar way, as a constant representing the impulse response at that time multiplied by the current. This results in:

| Red component | IR component |
|---|---|
| P1 = c1 · R | P1 = b5 · I |
| P2 = c2 · R | P2 = b6 · I |
| P3 = c3 · R | P3 = b7 · I |
| . | . |
| . | . |
| . | . |
| and so on. | |

Figure 4:
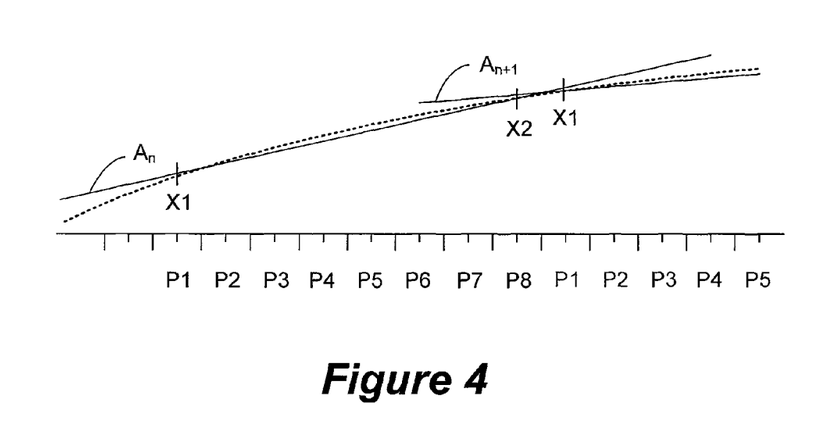
FIG. 4 shows how a piecewise linear approximation is applied to a signal representing ambient light.

The component of the signal representing the ambient light can be approximated for a sample period (P1 . . . . P8) by a linear approximation $A_n$ between points X1 and X2 as shown in FIG. 4, wherein point X1 is associated with sample time P1 and X2 is associated with sample time P8. A new approximation $A_{n+1}$ follows for the next eight samples as indicated in FIG. 4. The terms for ambient light only can, thus, be represented as:

$$P1 = X1$$
$$P2 = \frac{6}{7}X1 + \frac{1}{7}X2$$
$$P3 = \frac{5}{7}X1 + \frac{2}{7}X2$$
$$P4 = \frac{4}{7}X1 + \frac{2}{7}X2$$
$$\vdots$$
and so on.

The magnitude of the sample for the composite signal is the sum of all components. For instance:

$$P1 = 1 \cdot X1 + 0 \cdot X2 + k1 \cdot W1 + k7 \cdot W2 + k5 \cdot W3 + k3 \cdot W4 + c1 \cdot R + b5 \cdot I$$

The whole system can, thus, be represented in matrix form as:

$$\begin{bmatrix} P1 \\ P2 \\ P3 \\ P4 \\ P5 \\ P6 \\ P7 \\ P8 \end{bmatrix} = \begin{bmatrix} \frac{7}{7} & \frac{0}{7} & k1 & k7 & k5 & k3 & c1 & b5 \\ \frac{6}{7} & \frac{1}{7} & k2 & k8 & k6 & k4 & c2 & b6 \\ \frac{5}{7} & \frac{2}{7} & k3 & k1 & k7 & k5 & c3 & b7 \\ \frac{4}{7} & \frac{3}{7} & k4 & k2 & k8 & k6 & c4 & b8 \\ \frac{3}{7} & \frac{4}{7} & k5 & k3 & k1 & k7 & c5 & b1 \\ \frac{2}{7} & \frac{5}{7} & k6 & k4 & k2 & k8 & c6 & b2 \\ \frac{1}{7} & \frac{6}{7} & k7 & k5 & k3 & k1 & c7 & b3 \\ \frac{0}{7} & \frac{7}{7} & k8 & k6 & k4 & k2 & c8 & b4 \end{bmatrix} \cdot \begin{bmatrix} X1 \\ X2 \\ W1 \\ W2 \\ W3 \\ W4 \\ R \\ I \end{bmatrix}$$

or as a matrix equation as:

$$\hat{P} = \hat{K} \cdot \hat{L}$$

After measuring samples P1, P2, P3 . . . P8, the individual components of the composite signal can be isolated by solving the system of equations.

$$\hat{L} = \hat{K}^{-1} \cdot \hat{P}$$

In practice only the Red and IR components need to be solved as the other components are usually of no interest. This can be done by only computing the results for the bottom two rows of the system. The matrix of coefficients is a constant determined by the impulse response of the system. To solve the matrix for the Red and IR components, the inverse of the matrix only needs to be computed once for a particular front end filter 150, which can be done at start-up if a variable filter design is used or during the design of the system if the system uses a constant filter. Also an adaptive filter might be used. Then, the computation has to be performed after each adaptation.

As a result, the cable transients W can be eliminated from the signal on a real time basis. Stray capacitances in the cable will no longer be an issue. This also allows a front end to be designed with a much tighter anti-aliasing filter which will reduce noise and interference.

As mentioned above, a better performance can be achieved by increasing the number of samples per Red and IR measuring period. This oversampling will result in an over determined system that can be solved by using a pseudo-inverse to the constant matrix which gives a result that is a least squares fit to the sampled data. In general more over sampling will result in a more accurate measurement.

According to a further embodiment, the same technique can be used for more than two wavelength signals. This may also result in an over determined system that can be solved with a pseudo-inverse.

The above described concept is not limited to the error signals discussed, i.e., the ambient light signal and the cable transients. Other known error sources can be included in the matrix as discussed above.

Figure 5:
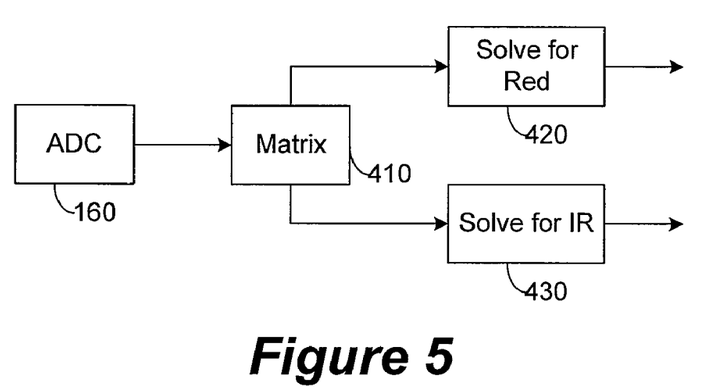
FIG. 5 shows how the signal is processed after it is digitized.

FIG. 5 shows an example of a system for solving the matrix equations. The data stream generated by the analog-to-digital converter 160 is fed to a matrix 410. Separate equations 420 and 430 for the Red signal and for the IR signal are computed to solve the matrix and generate the respective component signals for the Red and IR signals without the external error signals introduced to the signal fed to the analog-to-digital converter 160. The system shown can be easily implemented in a digital signal processor, microcontroller, or application specific integrated circuit (ASIC).

The invention, therefore, is well adapted to carry out the objects and attain the ends and advantages mentioned, as well as others inherent therein. While the invention has been depicted, described, and is defined by reference to particular preferred embodiments of the invention, such references do not imply a limitation on the invention, and no such limitation is to be inferred. The invention is capable of considerable modification, alteration, and equivalents in form and function, as will occur to those ordinarily skilled in the pertinent arts. The depicted and described preferred embodiments of the invention are exemplary only, and are not exhaustive of the scope of the invention. Consequently, the invention is intended to be limited only by the spirit and scope of the appended claims, giving full cognizance to equivalents in all respects.

What is claimed is:

1. A method for processing an analog composite signal in a system, the method comprising the steps of:
    receiving a composite signal comprising at least one first signal component and at least one interfering signal component;
    filtering the composite signal with a filter having a transfer function H(s); sampling the filtered composite signal in periodic intervals wherein each periodic interval comprises n samples;
    forming a matrix equation representing the composite signal wherein the matrix equation comprises a signal vector comprising the at least one first signal component and the at least one interfering signal component and a matrix comprising weighted coefficients, wherein the weighted coefficients for a transient interfering signal component are determined by the transfer function and a sample position within a periodic interval;
    solving the matrix equation to determine the at least one signal component;
    outputting the at least one signal component.

2. The method according to claim 1, wherein an interfering signal component is approximated by a linear approximation between a first and last sample of each periodic interval.

3. The method according to claim 1, wherein the system is an oximeter system comprising an oximeter sensor generating a Red signal component and an Infrared (IR) signal component as signal components and wherein an ambient light signal component and cable transients are interfering signal components.

4. The method according to claim 3, wherein the ambient light signal component is approximated by a linear approximation between a first and last sample of each periodic interval.

5. The method according to claim 3, wherein the weighted coefficients for the cable transients are determined by the transfer function and a sample position within a periodic interval.

6. The method according to claim 3, wherein the Red signal component and the IR signal component are timely separated within each periodic interval and the Red signal component and the IR signal component each comprise a predetermined signal length having an on and off transient.

7. The method according to claim 6, wherein the ambient light signal component is approximated by a linear approximation between a first and last sample of each periodic interval and the weighted coefficients for the cable transients are determined by the transfer function and a sample position within a periodic interval, and wherein a coefficient matrix comprises first and second coefficients for the linear approximation, switch on and switch off coefficients for the cable transients, a Red coefficient, and an IR coefficient.

8. A system for processing an analog composite signal comprising at least one first signal component and at least one interfering signal component, the system comprising:
    a filter having a transfer function H(s) receiving the composite signal and outputting a filtered composite signal;
    an analog-to-digital converter receiving the filtered composite signal and sampling the filtered composite signal in periodic intervals wherein each periodic interval comprises n samples;
    a signal processor receiving the sampled filtered composite signal, wherein the signal processor forms a matrix equation representing the composite signal wherein the matrix equation comprises a signal vector comprising the at least one first signal component and the at least one interfering signal component and a matrix comprising weighted coefficients, wherein the weighted coefficients for a transient interfering signal component are determined by the transfer function and a sample position within a periodic interval, wherein the signal processor is furthermore operable to solve the matrix equation to calculate the at least one signal component and to output the at least one signal component.

9. The system according to claim 8, wherein an interfering signal is approximated by a linear approximation between a first and last sample of each periodic interval.

10. The system according to claim 8, wherein the system is an oximeter system comprising an oximeter sensor generating a Red signal component and an Infrared (IR) signal component as signal components and wherein an ambient light signal component and cable transients are interfering signal components.

11. The system according to claim 10, wherein the ambient light signal component is approximated by a linear approximation between a first and last sample of each periodic interval.

12. The system according to claim 10, wherein the weighted coefficients for the cable transients are determined by the transfer function and a sample position within a periodic interval.

13. The system according to claim 10, wherein the Red signal component and the IR signal component are timely separated within each periodic interval and the Red signal component and the IR signal component each comprise a predetermined signal length having an on and off transient.

14. The system according to claim 13, wherein the ambient light signal component is approximated by a linear approximation between a first and last sample of each periodic interval and the weighted coefficients for the cable transients are determined by the transfer function and a sample position within a periodic interval, and wherein a coefficient matrix comprises first and second coefficients for the linear approximation, switch on and switch off coefficients for the cable transients, a Red coefficient, and an IR coefficient.

15. An oximeter system comprising:
    an oximeter sensor generating an output signal with a Red signal component and an Infrared (IR) signal component which are timely separated within a periodic interval wherein the Red signal component and the IR signal component each comprise a predetermined signal length having an on and off transient,
    a filter having a transfer function H(s) receiving a composite signal consisting of the oximeter sensor output signal and at least one interfering signal component, wherein the filter outputs a filtered composite signal;
    an analog-to-digital converter receiving the filtered composite signal and sampling the filtered composite signal in periodic intervals wherein each periodic interval comprises n samples;
    a signal processor receiving the sampled filtered composite signal, wherein the signal processor forms a matrix equation representing the composite signal wherein the matrix equation comprises a signal vector comprising the Red and IR signal components and the at least one interfering signal component and a matrix comprising weighted coefficients, wherein an ambient light signal component and cable transients are interfering signal components and wherein the weighted coefficients for the cable transients are determined by the transfer function and a sample position within a periodic interval, wherein the signal processor is furthermore operable to solve the matrix equation to calculate the Red and IR signal components and to output the Red and IR signal components.

16. The oximeter system according to claim 15, wherein the ambient light signal component is approximated by a linear approximation between a first and last sample of each periodic interval.

17. The oximeter system according to claim 15, wherein the ambient light component is approximated by a linear approximation between a first and last sample of each periodic interval and the weighted coefficients for the cable transients are determined by the transfer function and a sample position within a periodic interval, and wherein a coefficient matrix comprises first and second coefficients for the linear approximation, switch on and switch off coefficients for the cable transients, a Red coefficient, and an IR coefficient.

18. A method for processing an analog composite signal in an oximeter system, the method comprising the steps of:
    receiving a composite signal comprising at Red signal component and an infrared (IR) signal component from an oximeter sensor and at least one interfering signal component;
    filtering the composite signal with a filter having a transfer function H(s);
    sampling the filtered composite signal in periodic intervals wherein each periodic interval comprises n samples;
    forming a matrix equation representing the system wherein the matrix equation comprises a signal vector comprising the Red and IR signal component and the at least one interfering signal component and a matrix comprising weighted coefficients, wherein an ambient light signal component and cable transients are interfering signal components, wherein the ambient light is approximated by a linear approximation between a first and last sample of each periodic interval and wherein the weighted coefficients for the cable transients are determined by the transfer function and a sample position within a periodic interval;
    solving the matrix equation to calculate the Red and IR signal components;
    outputting the Red and IR signal components.

19. The method according to claim 18, wherein the Red signal component and the IR signal component are timely separated within each periodic interval and the Red signal component and the IR signal component each comprise a predetermined signal length having an on and off transient.

20. The method according to claim 19, wherein the ambient light is approximated by a linear approximation between a first and last sample of each periodic interval and the weighted coefficients for the cable transients are determined by the transfer function and a sample position within a periodic interval, and wherein a coefficient matrix comprises first and second coefficients for the linear approximation, switch on and switch off coefficients for the cable transients, a Red coefficient, and an IR coefficient.

* * * * *